United States Patent
Sahib et al.

(10) Patent No.: US 7,608,583 B2
(45) Date of Patent: Oct. 27, 2009

(54) PROCESS FOR THE EXTRACTION AND ISOLATION OF INSULIN FROM RECOMBINANT SOURCES

(75) Inventors: Maharaj K Sahib, Aurangabad (IN); Edupuganti B Raju, Aurangabad (IN); Umesh S Shaligram, Aurangabad (IN)

(73) Assignee: Wockhardt Limited (IN)

( * ) Notice: Subject to any disclaimer, the term of this patent is extended or adjusted under 35 U.S.C. 154(b) by 298 days.

(21) Appl. No.: 10/523,999

(22) PCT Filed: Nov. 14, 2003

(86) PCT No.: PCT/IB03/05197

§ 371 (c)(1),
(2), (4) Date: Feb. 9, 2005

(87) PCT Pub. No.: WO2004/050672

PCT Pub. Date: Jun. 17, 2004

(65) Prior Publication Data

US 2006/0167221 A1 Jul. 27, 2006

Related U.S. Application Data

(60) Provisional application No. 60/431,050, filed on Dec. 5, 2002.

(51) Int. Cl.
*A61K 38/28* (2006.01)
*C07K 1/14* (2006.01)
(52) U.S. Cl. .................. 514/3; 530/344; 530/303
(58) Field of Classification Search .......... None
See application file for complete search history.

(56) References Cited

U.S. PATENT DOCUMENTS 7,091,032 B2 * 8/2006 Annibali ............... 435/254.23

OTHER PUBLICATIONS

Willis "Expanded Bed Adsorption" Modern Drug Discov., 2001, 4, 43-44.*
Trinh et al. "Recovery of mouse endostatin produced by *Pichia pastoris* using expanded bed adsorption." Bioseparation, 2000, 9, 223-30.*
Scopes, Protein Purification: Principles and Practice, Springer, New York, 1994, pp. 157-171 and 85-93.*
Gerlough & Bates "The Purification and Some Properties of Insulin," J. Pharm. Exp. Therapeutics, 1932, vol. XLV, No. 1, pp. 19-51.*
Wang et al. ("Human Insulin from a Precursor Overexpressed in the Methylotropic Yeast *Pichia pastoris* and a Simple Procedure for Purifying the Expression Product," Biotechnology and Bioengineering, 2001, 73, 74-79).*

* cited by examiner

*Primary Examiner*—Cecilia Tsang
*Assistant Examiner*—Christina Bradley
(74) *Attorney, Agent, or Firm*—Bio Intellectual Property Services (Bio IPS LLC). O. M. (Sam) Zaghmout (57) ABSTRACT

The present invention relates to the extraction and isolation of insulins from recombinant sources, particularly those expressed in and secreted by yeasts. Organic solvents have been used to extract host surface bound forms of insulin polypeptide. In addition, procedures for combining the steps medium clarification, solvent extraction and chromatography, in order to effect the simultaneous isolation and purification of soluble and membrane bound forms of insulin, is disclosed.

8 Claims, 4 Drawing Sheets

SEQUENCE LISTING

```
<160> NUMBER OF SEQ ID NOS: 2

<210> SEQ ID NO 1
<211> LENGTH: 135
<212> TYPE: PRT
<213> ORGANISM: Homo sapiens

<400> SEQUENCE: 1

Met Arg Phe Pro Ser Ile Phe Thr Ala Val Leu Phe Ala Ala Ser
  1               5                  10                  15

Ser Ala Leu Ala Ala Pro Val Asn Thr Thr Glu Asp Glu Thr
                 20                  25                  30

Ala Gln Ile Pro Ala Glu Ala Val Ile Gly Tyr Ser Asp Leu Glu
                 35                  40                  45

Gly Asp Phe Asp Val Ala Val Leu Pro Phe Ser Asn Ser Thr Asn
                 50                  55                  60

Asn Gly Leu Leu Phe Ile Asn Thr Thr Ile Ala Ser Ile Ala Ala
                 65                  70                  75
```

```
                                   -continued

Lys Glu Glu Gly Val Ser Leu Asp Lys Arg Phe Val Asn Gln His
                80                  85                  90

Leu Cys Gly Ser His Leu Val Glu Ala Leu Tyr Leu Val Cys Gly
                95                 100                 105

Glu Arg Gly Phe Phe Tyr Thr Pro Lys Gly Ile Val Glu Gln Cys
               110                 115                 120

Cys Thr Ser Ile Cys Ser Leu Tyr Gln Leu Glu Asn Tyr Cys Asn
               125                 130                 135

<210> SEQ ID NO 2
<211> LENGTH: 408
<212> TYPE: DNA
<213> ORGANISM: Homo sapiens

<400> SEQUENCE: 2 atg aga ttt cct tca att ttt act gca gtt tta ttc gca gca tcc       45
Met Arg Phe Pro Ser Ile Phe Thr Ala Val Leu Phe Ala Ala Ser
  1               5                  10                  15 tcc gca tta gct gct cca gtc aac act aca aca gaa gat gaa acg       90
Ser Ala Leu Ala Ala Pro Val Asn Thr Thr Thr Glu Asp Glu Thr
                 20                  25                  30 gca caa att ccg gct gaa gct gtc atc ggt tac tca gat tta gaa      135
Ala Gln Ile Pro Ala Glu Ala Val Ile Gly Tyr Ser Asp Leu Glu
                 35                  40                  45 ggg gat ttc gat gtt gct gtt ttg cca ttt tcc aac agc aca aat      180
Gly Asp Phe Asp Val Ala Val Leu Pro Phe Ser Asn Ser Thr Asn
                 50                  55                  60 aac ggg tta ttg ttt ata aat act act att gcc agc att gct gct      225
Asn Gly Leu Leu Phe Ile Asn Thr Thr Ile Ala Ser Ile Ala Ala
                 65                  70                  75 aaa gaa gaa ggg gta agc ttg gat aaa aga ttt gtt aac caa cac      270
Lys Glu Glu Gly Val Ser Leu Asp Lys Arg Phe Val Asn Gln His
                 80                  85                  90 ttg tgt ggc tct cac ttg gtg gag gcg ttg tac ttg gtt tgc ggc      315
Leu Cys Gly Ser His Leu Val Glu Ala Leu Tyr Leu Val Cys Gly
                 95                 100                 105 gag cgt ggt ttc ttc tac act cct aag ggc atc gtt gag caa tgt      360
Glu Arg Gly Phe Phe Tyr Thr Pro Lys Gly Ile Val Glu Gln Cys
                110                 115                 120 tgt acc tcc atc tgt tcc ttg tac cag ctg gag aac tac tgt aac      405
Cys Thr Ser Ile Cys Ser Leu Tyr Gln Leu Glu Asn Tyr Cys Asn
                125                 130                 135 tga                                                              408
```

PROCESS FOR THE EXTRACTION AND ISOLATION OF INSULIN FROM RECOMBINANT SOURCES

CROSS-REFERENCE TO RELATED APPLICATIONS

This application claims the benefit of U. S. Provisional Application No. 60/431,050, filed Dec. 5, 2002; International Patent Application No. PCT/IB2003/005197, filed Nov. 14, 2003. The entire disclosure of these prior applications are hereby incorporated by reference.

BACKGROUND

The expression of polypeptides or proteins, by recombinant DNA methods is now possible by fairly well established methods. Briefly, it consists of cloning the gene encoding a protein of interest in a suitable heterlogous host such as $E.\ coli$, yeasts or mammalian cells and culturing the "recombinant" hosts in suitable culture conditions to induce the expression of the protein. The protein so expressed may either be retained intracellularly, or be secreted into the extracellular medium. The protein is then isolated and purified from the culture medium.

There are several methods available for the isolation and purification of proteins. Typically, when a protein is expressed, the culture medium containing the expressed protein is first "clarified" to get rid of the nonessential particulate components—cells and/or cell debris. This is then followed by one or more chromatographic procedures in which the particular protein is isolated from the clarified medium, the choice of the procedure depending upon the nature and properties of the protein to be purified.

The clarification of the culture medium, containing the expressed protein, is usually carried out by either centrifugation or filtration. But both these methods are greatly limited in terms of efficiency of clarification and the volume of culture medium that can be handled at any given time. More often then not, both these methods need to be employed, with the centrifugation step usually preceding the filtration process. This in turn adds considerably to the cost of the overall process as well as increase the processing time, the latter increasing the risk of protein degradation and hence product loss.

An important consideration during the isolation of proteins from the medium of expressing cells is the actual availability of the proteins in soluble form in the medium. Whether secreted into the extracellular medium, or retained inside the host cell, a considerable portion of the expressed protein may remain bound to the cells and cellular debris. Following medium clarification, these "bound" fractions would remain in the particulate residue and would be lost from the filtrate/supernatant that is being subjected to subsequent chromatographic steps. Thus the final yield of the protein would be much less then had the residue been subjected to separate extraction steps to extract the bound protein into solution. On the other hand, separate "extraction" steps, with different solvents, additives or pH conditions, followed by conventional clarification and chromatography would add to the overall number of "processing" steps, increasing the process time (and the consequent product degradation and loss) and costs of protein extraction and purification.

Thus it would be highly desirable if the steps of extraction, medium clarification and chromatography could be combined to isolate and purify an expressed protein. So far, however, most of the prior art dealing with protein purification procedures generally describe the more conventional chromatographic methods for protein isolation and purification.

For example, U.S. Pat. No. 4,616,078 and EP0197764 describe a process for separating impurities from "impure mixtures" containing proinsulin like material. The process consists of applying the mixture to a reverse phase macroporous acrylate ester copolymer resin and eluting the proinsulin like material under specific pH and buffer conditions.

Processes for the separation and isolation of basic protein from protein mixture, employing strong acid cation exchange chromatography and consisting of elution buffers containing a small amount of alkanol is described in U.S. Pat. No. 5,101,013 and EP0305760.

U.S. Pat. No. 5,245,008 and EP0474213 describe a process for the purification of insulin and/or insulin derivatives on lipophilically modified silica gel, employing aqueous, buffered solvents containing zwitterions, with the pH of the buffer in the vicinity of the isoelectric point of the insulin/insulin derivative.

U.S. Pat. No. 5,621,073 and EP0547544 describe a process for obtaining insulin, free of any acylated forms and proteases, by chromatography on a lipophilically modified silica gel.

Methods for improved separation and isolation of insulin from enzymatic cleavage reaction, using pressure stable acidic cation exchange resins are described in U.S. Pat. No. 5,977,297 and EP0849277.

U.S. Pat. No. 6,451,987 and EP1163261 describe various ion exchange chromatography methods employing an elution technique, which is a combination of elution in a solution comprising an organic modifier (such as $C_{1-6}$-alkanol, $C_{1-6}$ alkenol, urea, guanidine etc.) with subsequent elution in an aqueous solution.

U.S. Pat. No. 6,398,963, U.S. Pat. No. 6,428,707, EP0538467, WO9218237, WO9833572 and EP1003599 describe affinity based gel matrices, and methods for adsorption of a substance from a liquid sample, on an expanded bed mode. Finally, the paper of Scot Shepard, Gregory Boyd and Jeffrey Schrimsher (Bioseparation Vol 10 Pages 51-56), 2001 describe the use strong cation exchange expanded bed adsorption chromatography for the purification of two proteins, one with 183 amino acids and the other with 260 amino acids.

While some these patents describe methods for the isolation of insulin (and proteins in general) present in solution, they do not provide methods for isolating insulin that remain bound to cellular surfaces and debris of expressing cells. The processes described in most of the above patents presuppose the requirement of filtration/centrifugation, to get rid of the particulate residue, prior to chromatography of the clarified medium. Thus any bound insulin (or protein) would either be lost, or separate extraction of the particulate residue would be needed. As mentioned above, this would increase the number of processing steps, and the time required for isolation and extraction of the protein. On the other hand, the paper by Shepard et al. merely describes an expanded bed adsorption cation exchange chromatography of two proteins of 183 and 260 amino acid size, while the U.S. Pat. Nos. 6,398,963 and 6,428,707 describe the use of expanded bed chromatography (but in the form of affinity chromatography). There is no description of ways to effect the simultaneous isolation of "in solution", as well as particulate-residue-bound insulin. In the present invention, we disclose conditions for the extraction of insulin, to increase its recovery in solution, viz., in the liquid/buffer/medium in which the insulin expressing yeast culture has been suspended; and a procedure to combine extraction, medium clarification and chromatography, to effect the simultaneous isolation and purification of "in solution" as well as "particulate-residue-bound insulin". By insulin we mean "native" human insulin or the "native" insulin of non-human origin, such as those of porcine and bovine origin. The term "insulin" could also include "pro"insulins, "prepro"insulins, as well as insulin derivatives including those modified chemically and enzymatically. In addition, "insulin" could also include analogs with changes in the primary sequence. The analogues could be analogues of human insulin, as well as non-human insulin, such as porcine and bovine insulin.

DETAILED DESCRIPTION OF THE INVENTION

Figure 1:
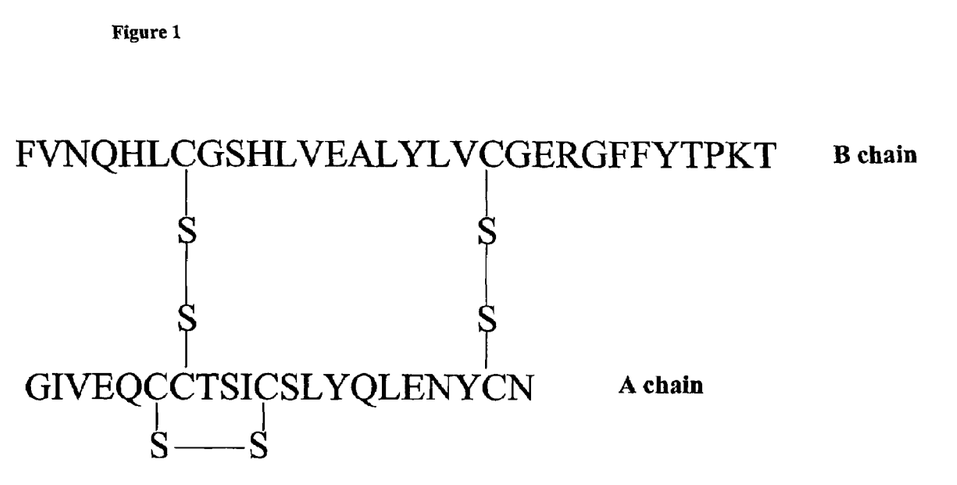
FIG. 1: Formula of human insulin.

In the present invention we disclose conditions wherein, when insulin expressing yeast cultures are resuspended under certain conditions, or in the presence of certain additives or organic solvents, the concentration of insulin in the supernatant, after centrifugation of the culture (or filtrate after filtration), is much higher then when the culture is resuspended in the absence of said conditions/additives/solvents. In other words, the insulin extracted in the presence of said additives/solvents/specific pH conditions is much higher then in their absence. This is perhaps due to the fact that a fraction of the protein expressed by the yeast culture is bound to the yeast cellular surface. Hence in the presence of said conditions, the insulin gets extracted into solution, whereas in their absence the insulin remains bound to the yeast and does not get extracted into solution. Though not wishing to being bound by theory, this is perhaps due to the presence of an "insulin binding protein" on the surface of yeast cells. In fact the paper of Muller et al (Biochemistry 1998, Vol. 37, pg. 8696-8704) describes the interaction of human insulin with a putative binding protein in the yeast *Saccharomyces cereviseae*. Furthermore, we also describe procedures for the isolation and purification of insulin, including the procedure to combine solvent extraction with medium clarification and chromatography to effect a rapid purification of insulin There are then two general embodiments to the present invention. In the first general embodiment we disclose conditions wherein, in the presence of water miscible organic solvents—including those that effect the dielectric constant and hydrophobicity of the medium, polar and ionized additives and specific pH conditions or combinations of the above, the concentration of insulin in solution would be higher then in their absence. By solution we mean in the liquid/buffer/medium in which the insulin expressing yeast culture has been suspended, as against particulate matter such as cells and cellular debris. While not wishing to be bound by theory, the effect of the solvents could be to reduce or weaken the interactions (such as hydrophobic interactions) between insulin and the yeast borne insulin-binding-protein. On the other hand charged and ionic additives may effect the interactions by weakening the charged interactions between the said proteins. Thus, when the insulin expressing yeast culture, in the presence of the above solvent/additives/pH conditions, has been subjected to, say centrifugation or filtration, the concentration of insulin in the supernatant or filtrate is much higher then when the cells were resuspended in the absence of said solvent/additives/pH conditions. Examples of solvent include, lower alcohols such as methanol, ethanol, butanol isopropanol etc; as well as solvents such as acetic acid, dimethyl formamide, dimethyl sulfoxide, acetonitrile, dioxan, ethylene glycol, propylene glycol etc. Examples of additives include salts such as sodium chloride (NaCl), calcium chloride ($CaCl_2$) etc., amino acids such as arginine, aspartic acid etc; as well as charged and polar compounds for example urea, guanidinum hydrochloride, polyethylene glycol etc. The pH at which the extractions were carried were from about 2.0 to about 5.0. The following examples would serve to illustrate this embodiment. We note however, that the examples should not be construed to restrict the scope of the embodiment or invention. We also reiterate that the protein specified in the examples does not limit the scope of the invention. As mentioned above, we prefer to use the term "insulin" rather generically. Thus in the present invention the term insulin would encompass the "native" protein consisting of B and A chains, consisting of 30 and 21 amino acids respectively, with two interchain and one intrachain disulfide bonds. The "native" insulin could be of human and non-human origin (such as those of porcine and bovine origin. The formula in FIG. 1 is an example of insulin of human origin). Insulin would also refer to "pro"insulins and "prepro"insulins—which carry additional amino acids. The additional amino acids in pro and preproinsulins could aid the correct folding of the protein, or direct the expressed protein into the extracellular medium, or even aid the purification of the protein. Insulin would also include derivatives such as those obtained by chemical and/or enzymatic modifications. In addition insulin would include analogs with primary sequence changes. Such changes could be amino acid replacements, removal of one or more amino acids etc; such as one represented as B(1-29)-A(1-21), where B(1-29) is the B-chain peptide from amino acid 1 to amino acid 29 of the "native" insulin B chain and A(1-21) is the A-chain peptide from amino 1 to amino acid 21 of the "native" insulin A chain. In B(1-29)-A(1-21), the amino acid 29 of the B chain is connected by means of a peptide bond to amino acid 1 of the A chain.

Construction of the Recombinant Vector Carrying the Insulin Polypeptide Gene

In the specific examples below, the sequence of the insulin polypeptide used is provided in the Seq ID1. Seq ID2 is the DNA sequence corresponding to that of amino acid sequence in Seq ID1.

In the seq ID1, the peptide region from amino acid 1 to 85 is the mating factor alfa (MFα) leader peptide from *Saccharomyces cerevisiae* that is required for the secretion of the expressed product into the extracellular medium. The MFα leader sequence carries a Kex2 protease site and is removed by yeast processing enzyme Kex2 protease just prior to secretion. Thus the insulin polypeptide that is eventually secreted is B(1-29)-A(1-21), where B(1-29) is the B-chain peptide from amino acid 1 to amino acid 29 of the "native" insulin B chain and A(1-21) is the A-chain peptide from amino acid 1 to amino acid 21 of the "native" insulin A chain. In B(1-29)-A(1-21), the amino acid 29 of the B chain is connected by means of a peptide bond to amino acid 1 of the A chain. In the present instance, the B and A chains are the those of human origin. B(1-29)-A(1-21) corresponds to amino acid sequence stretch 85-135 in Seq ID 1.

Figure 2:
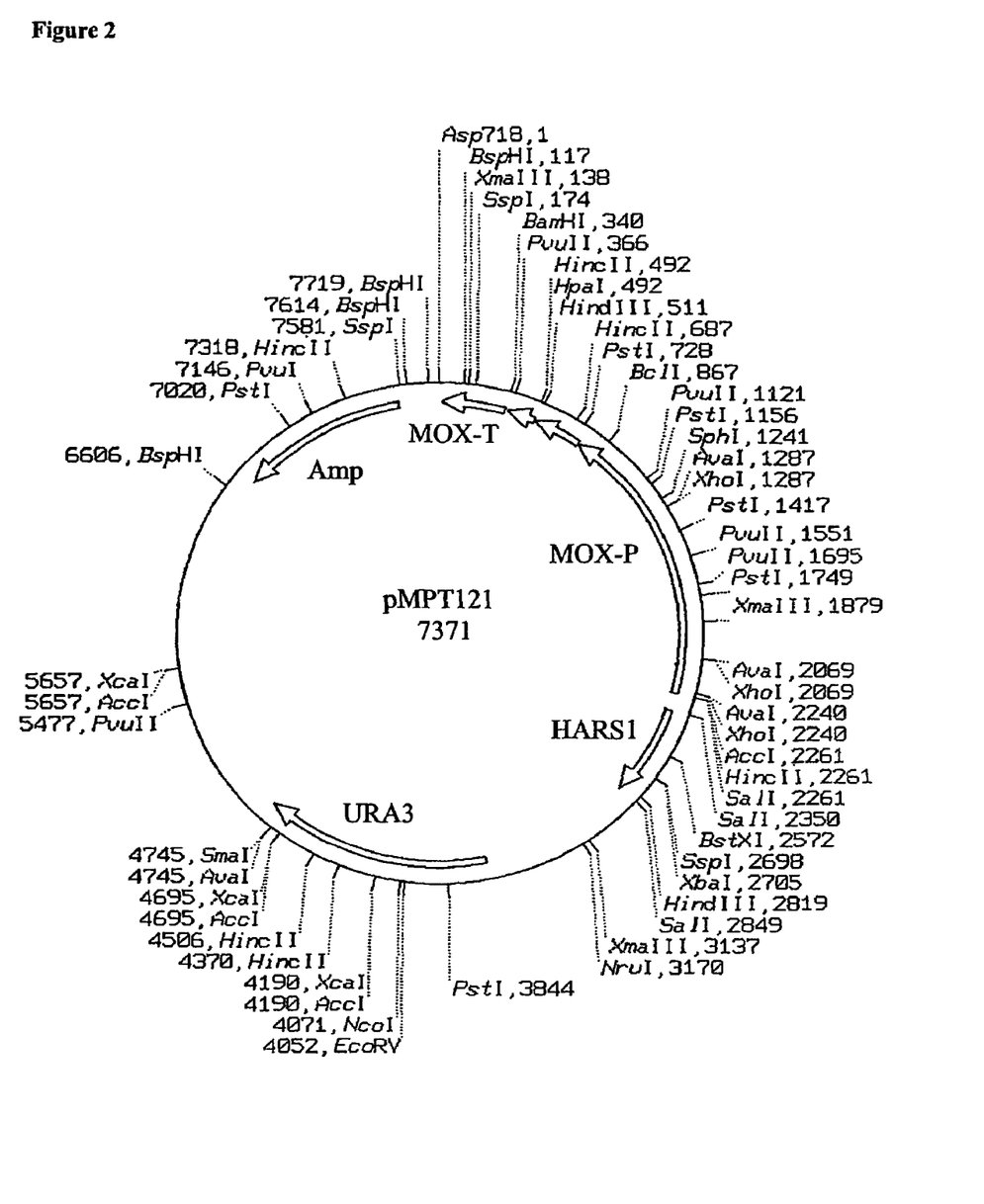
FIG. 2: The expression vector used for the expression and secretion of Insulin polypeptide in the present invention. MOX-promoter refers to the alcohol inducible promoter methanol oxidase promoter, MOX-T refers to the methanol oxidase terminator. Amp refers to the ampicillin resistance conferring gene and URA3 is the yeast auxotropic selection marker.

The gene, as represented in Seq ID2, was constructed taking into account the codon usage by the host (in the examples below, the yeast strain *Hansenula polymorpha*). The DNA construct comprising the gene possess, in addition, two restriction enzymes—E. coRI and BamH1—on either sides of the gene. The DNA construct so obtained was cloned into the EcoRI and BamH1 restriction enzyme sites of the plasmid expression vector pMPT121 (FIG. 2) by methods well known to those of ordinary skill in the art ("Molecular Cloning: A Laboratory Manual" by J. Sambrook, E. F. Fritsch and T. Maniatis, II edition, Cold Spring Harbour Laboratory Press, 1989) and transformed into *E. coli* hosts by methods also well known to those skilled in the art ("Molecular Cloning: A Laboratory Manual" by J. Sambrook, E. F. Fritsch and T. Maniatis, II edition, Cold Spring Harbour Laboratory Press, 1989)

The pMPT121 plasmid expression vector is based on a pBR322 plasmid and contains the following elements:
- standard *E. coli* pBR322 skeleton including *E. coli* origin of replication (ori).
- ampicilin resistance gene for selection of transformed *E. coli*.
- auxotrophic selective marker gene complementing the auxotrophic deficiency of the host—*Hansenula polymorpha*, (*H. polymorpha*) (URA3 gene).
- *H. polymorpha* Autonomously Replicating Sequence (HARS).
- an expression cassette containing the MOX promoter and the MOX terminator for insertion of the gene construct and controlling the expression of the cloned heterologous polypeptides in the said yeast strain.

Individual *E. coli* clones carrying the recombinant plasmids were cultured and the plasmids isolated by methods well known in the art ("Molecular Cloning: A Laboratory Manual" by J. Sambrook, E. F. Fritsch and T. Maniatis, II edition, Cold Spring Harbour Laboratory Press, 1989). The isolated recombinant plasmids were then confirmed to be carrying the above Seq ID2, by DNA sequencing.

Transformation of a Yeast Strain with the Recombinant Vectors Carrying the Insulin Polypeptide Gene The recombinant plasmids obtained as above was transformed into the yeast strain *H. polymorpha* (which is an ura3 auxotrophic mutant deficient in orotidine-5'-phosphate decarboxylase) by methods known in the art (*Hansenula polymorpha*: Biology and Applications, Ed. G. Gellissen. Wiley-VCH, 2002). The resulting recombinant clones were then further used for the expression of the insulin polypeptide Expression of the Insulin Polypeptide in Yeast The yeast transformants thus obtained were used for the expression of the insulin polypeptide. The expression conditions were:

a) Preculture:

Single clones, each carrying the expression vector carrying the DNA sequences encoding the insulin polypeptide (viz. Seq ID2 corresponding to Seq ID1) were inoculated into 100 ml of autoclaved 2×YNB/1.5% glycerol medium in a 500 ml shake flask with baffles. The composition of the 2×YNB/1.5% is 0.28 g yeast nitrogen base, 1.0 g ammonium sulfate, 1.5 g glycerol and 100 ml water. The cultures were incubated for about 24 h at 37° C. with 140 rpm shaking until an O.D$_{600}$ of 3-5 is reached b) Culture:

2×450 ml of autoclaved SYN6/1.5% glycerol media in 2×2000 shake flasks with baffles were inoculated with 20-50 ml of each of the above preculture. The cultures were then incubated for 36 h at 30° C. and 140 rpm. The composition of the SYN6/1.5% glycerol medium is NH$_4$H$_2$PO$_4$—13.3 g, MgSO$_4$×7H$_2$O—3.0 g, KCl—3.3 g, NaCl—0.3 g, glycerol—15.0 g, in water 1000 ml. The media was further supplemented with CaCl$_2$, microelements, vitamins and trace elements.

c) Fermentation:

10L of SYN6 medium (composition as of SYN6/1.5% glycerol but not containing glycerol, but containing 1% soya oil) was autoclaved in a fermentor for 20 min. at 121° C. After autoclaving, the temperature, pH, aeration and agitation were set to the desired values (pH to 4.0, agitation to 400 rpm, aeration to 1 vvm). The fermentor was inoculated with the seed culture and fermentation continued for additional 5 days at dissolved oxygen concentration (DO) 50%. Samples may be collected at regular intervals and at the end of fermentation to check for growth, product concentration, pH and state of the cells.

In the following examples we discuss various conditions in which, in the presence of certain solvents/additives/pH conditions or combinations thereof, the concentration of insulin in solution would be higher then in their absence. Thus, at least some of the presumably "bound" forms of the insulin polypeptides—those present on the particulate cell/cellular debris—are extracted into solution in the presence of the said conditions.

These processes or procedures may generally be described as "extractions". In the examples below, the various volumes of the insulin polypeptide containing culture broth used for the extractions are obtained at the end of the fermentation described above.

EXAMPLE 1

Effect of Organic Solvents and Additives on Insulin Polypeptide Extraction at Various pH Conditions Equal volumes of fermentation culture broth, containing the insulin polypeptide, were adjusted to either pH 2.0, 3.0 or 4.0, aliquoted into different flasks and treated with different additives or organic solvents. The final concentrations of the additives/organic solvents were 100 mM arginine, 10 mM aspartic acid, 100 mM CaCl$_2$, 20% isopropanol, 20% dioxan and 6M urea. The samples were incubated at room temperature for 10 min. 2 ml cultures were then clarified by centrifugation and the supernatants quantified for insulin polypeptide by RP-HPLC (Table 1). "Control" refers to samples, at the respective pH, but free of any of the above mentioned additives.

TABLE 1

| Culture condition | Insulin polypeptide (mg/L) at pH 2.0 | Insulin polypeptide (mg/L) at pH 3.0 | Insulin polypeptide (mg/L) at pH 4.0 |
|---|---|---|---|
| Control | 509 | 391 | 215 |
| Culture containing 100 mM arginine | 555 | 409 | 285 |
| Culture containing 100 mM aspartic acid | 569 | 402 | 210 |
| Culture containing 100 mM CaCl$_2$ | 570 | 452 | 362 |
| Culture containing 20% isopropanol | 591 | 557 | 402 |
| Culture containing 20% Dioxan | 621 | 604 | 518 |
| Culture containing 6M Urea | 647 | 615 | 585 |

From Table 1 it is clear that in the presence of the additives—arginine, aspartic acid, CaCl$_2$, isopropanol, dioxan and urea—the yields of the insulin polypeptide were much higher then in the controls at all three pH values.

EXAMPLE 2

Effect of Organic Solvents on Insulin Polypeptide Extraction at pH 3 and 4

20 ml aliquotes of fermentation culture broth were individually mixed with various organic solvents (4 ml each) and the pH adjusted to either 3 or 4. The mixtures were incubated at room temperature for 10 min, centrifuged and the supernatant quantified for insulin polypeptide by RP-HPLC. The data is presented in table 2.

TABLE 2

|  | Insulin polypeptide (mg/L) at pH 4.0 | Insulin polypeptide (mg/L) at pH 3.0 |
| --- | --- | --- |
| Culture + MilliQ water (control) | 280 | 595 |
| Culture + 20% methanol | 479 | 680 |
| Culture + 20% ethanol | 570 | 704 |
| Culture + 20% t-butanol | 647 | 735 |
| Culture + 20% acetonitrile | 648 | 746 |
| Culture + 20% dimethylformamide | 743 | 779 |
| Culture + 20% dimethylsulfoxide | 679 | 770 |
| Culture + 20% ethylene glycol | 578 | 719 |
| Culture + 20% propylene glycol | 619 | 729 |
| Culture + 20% acetic acid | 649 | 738 |

From Table 2 it is clear that in the presence of the additives—methanol, ethanol, t-butanol (tertiary-butanol), acetonitrile, dimethylformamide, dimethylsulfoxide, ethyleneglycol, propyleneglycol, acetic—the yields of the insulin polypeptide were much higher then in the controls at pH 3 as well as pH 4.

EXAMPLE 3

Effect of Isopropanol Concentration on Insulin Polypeptide Extraction

In the present example, we evaluated the effect of isopropanol concentration on the extraction of insulin polypeptide. Equal volumes of fermentation culture broth, containing the insulin polypeptide, were incubated with different concentrations of 10 isopropanol at pH 3.0 for 10 min. The final volumes were maintained equal with milliQ water. 2 ml of the test samples were then centrifuged and the supernatant quantified for insulin polypeptide by RP-HPLC. (The cell concentration of each sample was 15% volume/volume). The data is presented in table 3.

TABLE 3

| Concentration of Isopropanol in culture broth as % volumes | Insulin polypeptide concentration (mg/L) |
| --- | --- |
| 0 | 300 |
| 10 | 369 |
| 20 | 438 |
| 30 | 462 |

TABLE 3-continued

| Concentration of Isopropanol in culture broth as % volumes | Insulin polypeptide concentration (mg/L) |
| --- | --- |
| 40 | 438 |
| 50 | 448 |

EXAMPLE 4

Effect of pH on Insulin Polypeptide Extraction in the Presence and Absence of Isopropanol (20%)

In this example we disclose the effect of pH on the extraction of the insulin polypeptide by isopropanol. Equal volumes of fermentation culture broth containing the insulin polypeptide were incubated for 10 min at different pH, with and without isopropanol. 2 ml samples were centrifuged and the supernatant quantified for insulin polypeptide by RP-HPLC. The data is presented in table 4.

TABLE 4

| pH | Culture broth - Insulin polypeptide (mg/L) | Culture broth containing 20% isopropanol - Insulin polypeptide (mg/L) | % Difference in Insulin polypeptide concentration due to isopropanol |
| --- | --- | --- | --- |
| 2.0 | 476 | 534 | 12 |
| 2.5 | 459 | 524 | 14.2 |
| 3.0 | 450 | 513 | 14 |
| 3.5 | 411 | 494 | 20 |
| 4.0 | 381 | 453 | 18.9 |
| 4.5 | 333 | 399 | 19.8 |
| 5.0 | 313 | 375 | 19.8 |

EXAMPLE 5

Double Extraction with 20% Isopropanol

Equal volumes of fermentation culture broth containing the insulin polypeptide were diluted, either with isopropanol (to get a final concentration of 20% isopropanol) or without isopropanol (control), with pH at 2.0 and incubated at room temperature for 10 min. Samples were then centrifuged and the respective supernatants completely decanted. The decanted supernatants, the control and isopropanol treated, were then quantified for insulin polypeptide by RP-HPLC. The pellet of the sample treated with isopropanol was again resuspended in a solution containing 20% isopropanol (the volume being maintained) at pH 2.0 and incubated for 10 min at room temperature. This sample was then again centrifuged and the supernatant quantified for insulin polypeptide by RP-HPLC. The data is presented in table 5.

TABLE 5

|  | Insulin polypeptide (mg/L) | % increase in Insulin polypeptide over control |
| --- | --- | --- |
| Culture (control) | 681 | N/A |
| Culture diluted with isopropanol at pH 2.0 (extraction) | 947 | 39 |

TABLE 5-continued

|  | Insulin polypeptide (mg/L) | % increase in Insulin polypeptide over control |
|---|---|---|
| Extraction of cells with additional 20% isopropanol at pH 2.0 (re-extraction) | 150 | *61 |

*61% is the increase of total insulin polypeptide yielded from the two isopropanol extraction (calculated by (150 + 947) − 681 = 416; 416/681 = 61%

EXAMPLE 6

Sequential Extraction of the Insulin Polypeptide under Different Conditions

In this example we evaluate the yield of insulin polypeptide when subjected to serial extractions with different additives and isopropanol.

30 ml of fermentation culture broth containing the insulin polypeptide, each in two separate falcon tubes and pH adjusted to 4.0, were first analyzed, by RP-HPLC, to contain 524 mg/L insulin polypeptide in solution. The samples were then centrifuged and the supernatant decanted (viz. 22 ml containing 500 mg/L insulin was removed).

The cell pellet of one of the samples was then sequentially washed with 20 ml solution of, citrate buffer (pH 4.0), citrate buffer with 1M NaCl, 20% isopropanol, 5M urea at pH 4 and finally 5M Urea at pH 2.0. For the second sample, the same set of solutions were used, but the washing/extraction steps with solutions containing 1M NaCl and 20% isopropanol were reversed.

In case of both the samples, the amount of insulin polypeptide extracted during each washing step was estimated from the corresponding supernatant by RP-HPLC. The data is presented in table 6.

TABLE 6

| Sequential extraction Case I | Insulin polypeptide in supernatant mg/L | Sequential extraction Case II | Insulin polypeptide in supernatent mg/L |
|---|---|---|---|
| Cell wash with citrate buffer at pH 4.0 | 14.6 | Cell wash with citrate buffer | 16.4 |
| Cell wash with citrate buffer containing 1M NaCl at pH 4.0 | 16.7 | Cell wash with citrate buffer containing 20% 2-propanol | 15.4 |
| Cell wash with citrate buffer containing 20% 2-propanol at pH 4.0 | 51.3 | Cell wash with citrate buffer containing 1M NaCl | 26.7 |
| Cell wash with citrate buffer containing 5M urea at pH 4.0 | 45.9 | Cell wash with citrate buffer containing 5M urea at pH 4.0 | 82.5 |
| Cell wash with 5M urea at pH 2.0 | 36.6 | Cell wash with 5M urea at pH 2.0 | 30.6 |
| Proinsulin extracted from cells (Cumulative) | 165.1 | Proinsulin extracted from cells (Cumulative) | 171.6 |

Taking into account the 524 mg/L insulin present in the "first" supernatant, viz before the extractions, the total insulin polypeptide isolated at the end of the extractions exceeds 650 mg/L. Thus a significant portion (at least 28%) of the insulin polypeptide that is expressed by the yeast, remains bound to the cellular surface. These bound forms are extracted only after subjecting the "particulate" material of the culture to the different extraction procedures.

EXAMPLE 7

Effect of Organic Solvents and Additives on Insulin Binding at pH 3.0

This example provides data underscoring the fact that insulin polypeptide can indeed bind to yeast cellular surface. The experiment essentially consists of resupending insulin polypeptide with a yeast strain, and then determining the concentration of the insulin polypeptide remaining in the supernatant after a short incubation period. The yeast culture used, in the present example *H. polymorpha*, does not express insulin polypeptide, and the insulin polypeptide was added externally. The yeast cell concentrate was first collected after cross flow filtration, washed with milliQ water and incubated with a specific amount of insulin polypeptide in the presence and absence of organic solvents or additives. The samples were incubated at pH 3.0 for 10 min at room temperature. Subsequently, 2 ml of each sample was centrifuged and the insulin polypeptide in the supernatants quantified by RP-HPLC. The data are presented in table 7.

TABLE 7

| Condition | Insulin polypeptide concentration (mg/L) | % bound Insulin polypeptide |
|---|---|---|
| Insulin polypeptide solution without cells (control), pH 3.0 | 1084 | |
| Cells plus containing insulin polypeptide, pH 3.0 | 484 | 55 |
| Cells plus containing insulin polypeptide and 8M urea, pH 3.0 | 928 | 14.4 |
| Cells plus containing insulin polypeptide and 20% Isopropanol, pH 3.0 | 875 | 15.7 |
| Cells plus containing insulin polypeptide and 10% Dioxane, pH 3.0 | 643 | 44 |

From table 7, it is clear that when the insulin polypeptide solution is incubated with cells in the absence of any additives, a large percentage (more the 50%) of the insulin polypeptide gets bound to the cell surface (or is "lost" from the supernatant). But in the presence of additives urea, isopropanol, dioxane the percentage of bound insulin is considerably less.

In the second general embodiment of the present invention we have combined the steps of water soluble solvent extraction, medium clarification and chromatography to effect the extraction and purification of the expressed insulin polypeptide.

As discussed in earlier sections, a key feature, and a first step, towards protein isolation and purification from the medium of expressing cells and cultures is the clarification of the medium to remove any particulate components. This is then followed by one or more chromatographic procedures to isolate and purify the protein from the clarified medium. Typically, medium clarification and chromatography are distinct steps, employing distinctly different procedures and equipment. Thus, typically, culture broth containing the expressed protein is, at the end of fermentation, first subjected to filtration and or centrifugation, to clarify the medium. The clarified medium is then subjected to one or more chromatographic procedures to isolate the protein. These separate steps of medium clarification, followed by chromatography, greatly add to the cost as well as time required for the isolation of a protein. The time factor is the more crucial, since a prolonged lag time between medium clarification and the first chromatography greatly increases the risk of protein degradation and yield loss. The loss in yield may be further compounded, if a fraction of the expressed protein, as in the case of insulin, is bound to the cells expressing the same. Thus upon medium clarification, this fraction is retained with the particulate residue and is "lost" as far as further chromatographic purification is concerned. Isolating such bound fraction would require additional extraction steps, with solvents, salts or other additives, pH conditions etc. The extracts then have to be subjected to chromatography along with the original clarified medium.

Figure 3:
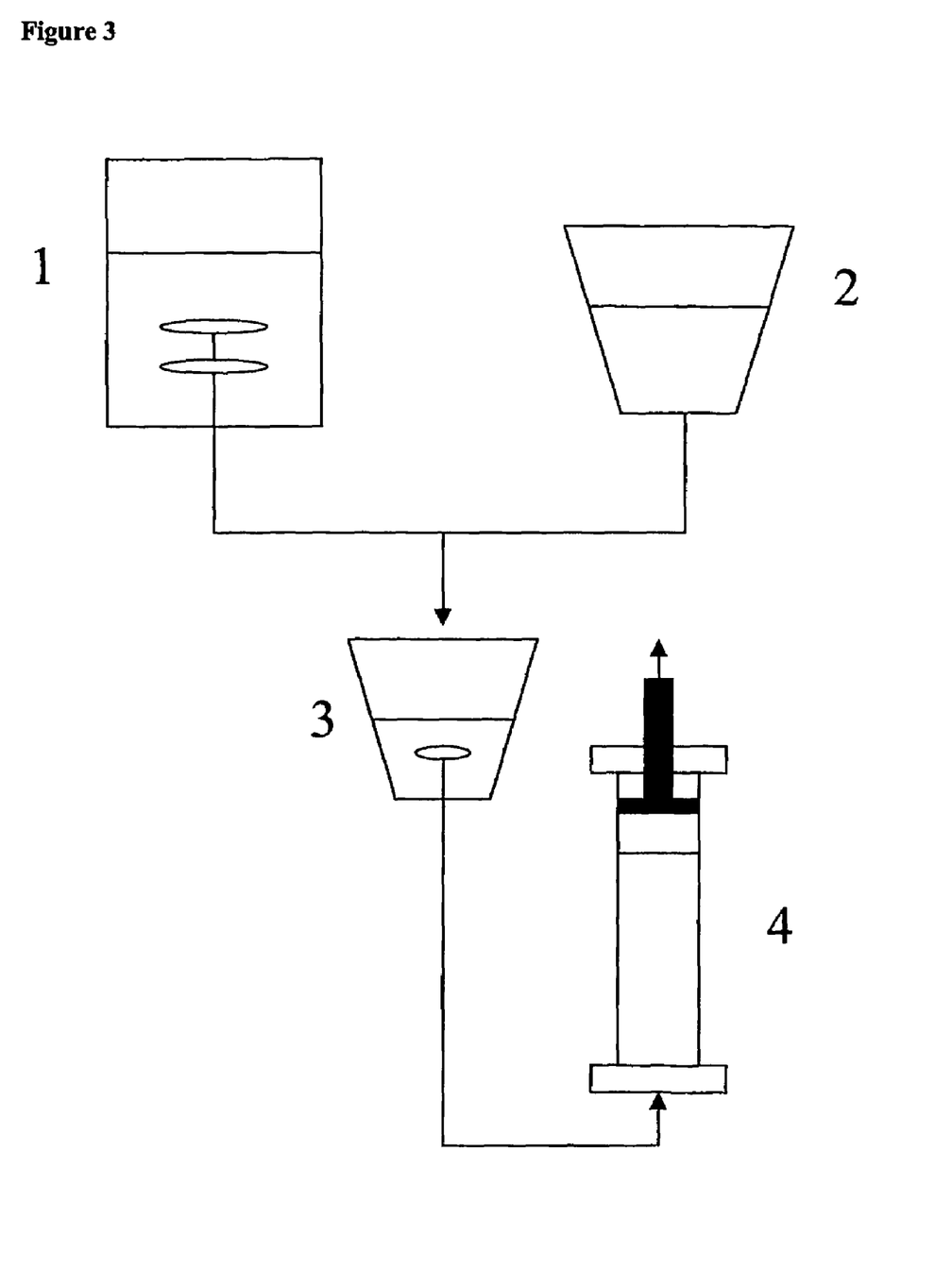
FIG. 3: Schematic representation of the isolation and purification of the insulin polypeptide by isopropanol extraction and expanded bed chromatography. Unit 1 is the fermenter vessel containing fermentation culture of insulin polypeptide expressing yeast culture. Unit 2 carries the diluent buffer having organic solvent. The fermentation broth is mixed with the diluent buffer in unit 3. The mixture of fermentation broth and organic solvent containing buffer is continuously fed to the chromatography column containing the Streamline-SP cation exchange chromatography resin in the expanded mode (unit 3)
Figure 4:
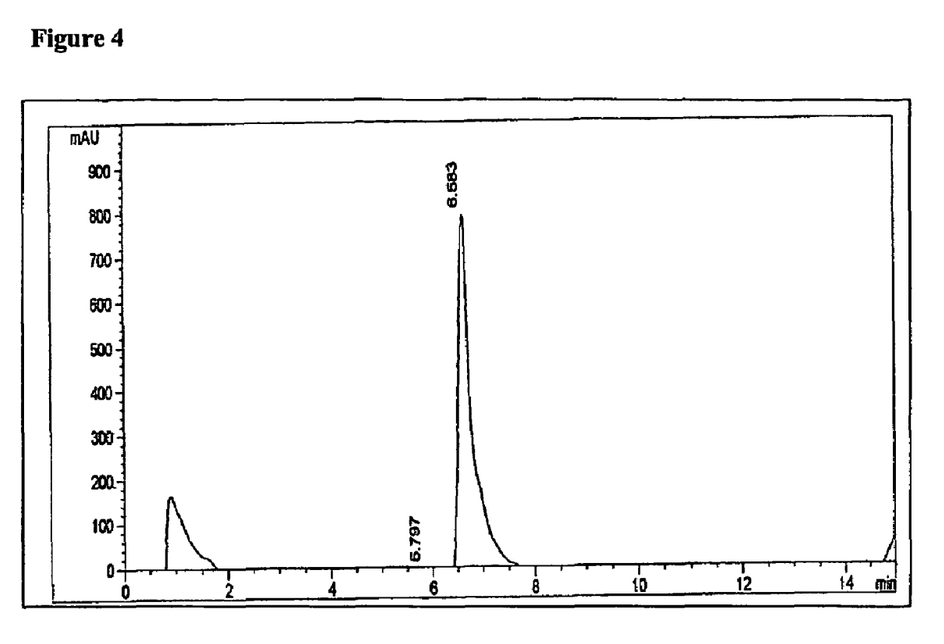
FIG. 4: Purity of the insulin polypeptide isolated employing the procedure described in Example 7. The small peak at about 1 min is related to non-proteinous material eluting at solvent front.

In this second embodiment we have combined the steps of solvent extraction, medium clarification and chromatography to isolate and purify the expressed insulin polypeptide. Briefly, in this embodiment we have used the principle of expanded bed ion exchange chromatography to purify insulin polypeptide. Expanded bed chromatography consists of a single pass operation in which the desired protein is purified from crude, particulate containing fermentation broth without the need for separate clarification and concentration. In a specific embodiment, the fermentation broth—medium plus particulate components (cells/cellular debris)—containing insulin polypeptide was mixed with a water soluble solvent in a buffer at particular pH (example, isopropanol at 20% final concentration) and continuously fed to an expanded bed chromatography column packed with an ion exchange resin, such as the Streamline SP cation exchange resin that had been expanded three fold. Treatment with the organic solvent results in the extraction of insulin polypeptide bound to the particulate residue, and which is then subjected to chromatography, along with the pre-existing in-solution insulin polypeptide. Since this results in the simultaneous isolation and purification of "in solution" as well as particulate-residue-bound insulin, it results in higher final yields of purified protein then alternative procedures, such as: 1) Normal "packed bed" chromatography, in which the medium must first be clarified by filtration and then the filtrate subjected to normal chromatography, and 2) Expanded bed chromatography, in which the fermentation broth is directly fed into an expanded bed chromatography column, but without any addition of organic solvent. The procedure is described schematically in FIG. 3. Some of the prior art, dealing with such alternative methods have been discussed briefly in the background section of this application. It may be noted that the combining of the steps of solvent extraction, medium clarification and chromatography (in the expanded bed mode) of the present embodiment also results in insulin polypeptide of very high purity, as seen in FIG. 4. The following examples describe in detail the present embodiment of expanded bed chromatography simultaneous with water-soluble solvent extraction. The yields of insulin polypeptide obtained from the present embodiment are also compared with those obtained by alternative procedures, viz., normal chromatography and expanded bed chromatography (without simultaneous solvent extraction). It should be mentioned that the source for insulin polypeptide is the recombinant *Hansenula polymorpha* that had been transformed with a plasmid expression vector carrying the insulin polypeptide gene. Details regarding the nature of the expression system, the fermentation conditions for insulin polypeptide expression etc, have been described in previous sections and is incorporated herein by reference.

EXAMPLE 8

Insulin Polypeptide Capture Employing Tangential Flow Filtration Followed by Cation Exchange Chromatography a) Culture Medium Clarification and Concentration by Filtration:

At the end of fermentation 1 liter culture containing 385 mg insulin polypeptide in solution (estimated by RP-HPLC) was cooled to 10° C. and passed through a 0.22 µm, Sartocon Hydrosart filtration cassette from Sartorius (surface area 50 cm$^2$). 550 ml filtrate (filtrate 1) containing insulin polypeptide was collected at 1 bar transmembrane pressure. The cell concentrate was diluted with 500 ml citrate buffer at pH 3.0. The filtration process was continued, to collect another 500 ml filtrate (filtrate 2) and the resulting cell concentrate was again diluted with 500 ml citrate buffer at pH 3.0. A further 500 ml filtrate was collected (filtrate 3). All three filtrates were pooled and quantified for insulin polypeptide by RP-HPLC. The total amount of insulin polypeptide in the pooled filtrates was 327 mg corresponding to 85% of the total amount estimated prior to filtration.

b) Insulin Polypeptide Isolation on Cation Exchange Chromatography:

The above pooled clarified filtrate containing a total of 327 mg insulin polypeptide, was diluted two fold with 20 mM citrate buffer, pH 3.0 and subjected to cation exchange chromatography. A packed chromatography column (26 mm×50 nm) containing 26 ml cation exchange SP-sepharose fast flow resin was employed. The diluted supernatant was applied to the column, which was equipped with an online UV monitor at 280 nm. After loading, the column was washed with 5 column volumes of 20 mM citrate buffer pH 3.0. The insulin polypeptide was eluted with 100 mM tris HCl buffer at pH 7.5. The insulin polypeptide was precipitated from the eluate at pH 6.0 in presence of Zinc ions. From a filtrate containing a total 327 mg of insulin polypeptide, and that had been subjected to chromatography (followed by Zn precipitation), 277 mg of insulin polypeptide was obtained at the end of the chromatography and Zn precipitation. Thus the yield is 88%. Also, the cumulative yield, beginning with clarification, followed chromatography and Zn precipitation is 75%.

The procedure for the precipitation of the insulin polypeptide: $ZnCl_2$ may be added to the chromatography eluate (1:1 w/w with respect to the insulin polypeptide) and the pH adjusted to 6.0 with ammonia solution. The suspension may then left in the refrigerator (8° C.) for at least 6 h. The solution may then centrifuged at 5000 rpm for 10 min and the supernatant decanted and the pellet dried under vacuum. The pellet may then be dissolved in dilute acidic buffer and the insulin polypeptide quantified by RP-HPLC.

EXAMPLE 9

Insulin Polypeptide Isolation from Culture Broth Employing Expanded Bed Cation Exchange Chromatography At the end of fermentation, 1 liter culture containing 336 mg of insulin polypeptide in solution, was diluted two fold with 20 mM citrate buffer, pH 3 and fed to an expanded bed chromatography column, Streamline 25 (25 ml×100 mm dimensions), packed with 75 ml Streamline-SP cation exchange chromatography resin (Amersham Pharmacia Biotech) and equipped with a solvent delivery system and online UV detection at 280 nm. The loading was carried out at a flow rate of about 100 cm/h, (three fold bed expansion of the resin). The column was then washed with 10 column volumes of 20 mM citrate buffer at pH 3.0. The resin bed was then allowed to settle. The insulin polypeptide was then eluted with 100 mM Tris HCl pH 7.5. The eluate was collected as a single fraction and the insulin polypeptide was precipitated from the eluate at pH 6.0 in the presence of Zinc ions. The precipitation and subsequent drying and dissolution was carried out as described in the earlier section and incorporated herein by reference. The insulin polypeptide was quantified by RP-HPLC.

From a fermentation broth containing a total 336 mg of insulin polypeptide in solution, and that had been subjected to chromatography (followed by Zn precipitation), 288 mg of insulin polypeptide was obtained at the end of the chromatography and Zn precipitation. Thus the yield is 86% (viz. the cumulative yield, beginning with the expanded bed chromatography and followed by Zn precipitation).

EXAMPLE 10

Extraction with Isopropanol Followed by Isolation of Insulin Polypeptide from Fermentation Culture Broth Employing Expanded Bed Cation Exchange Chromatography At the end of fermentation, 1 liter culture broth containing 335 mg of insulin polypeptide in solution was diluted two fold with 20 mM citrate buffer, pH 3 containing isoproponal at a final concentration of 20% and directly fed to an expanded bed chromatography column, Streamline 25 (25 mm×100 mm dimensions), packed with 75 ml Streamline-SP cation exchange chromatography resin (Amersham Pharmacia Biotech) and equipped with a solvent delivery system and online UV detection at 280 nm. The loading was carried out at a flow rate about 100 cm/h (three fold bed expansion of the resin). The column was then washed with 10 column volumes of 20 mM citrate buffer at pH 3.0. The resin bed was then allowed to settle. The insulin polypeptide was then eluted with 100 mM Tris HCl pH 7.5. The eluate was collected as a single fraction and the insulin polypeptide was precipitated from the eluate at pH 6.0 in presence of Zinc ions. The precipitation and subsequent drying and dissolution was carried out as described in the earlier section and incorporated herein by reference. The concentration of insulin polypeptide was estimated by RP-HPLC.

From a fermentation broth containing a total 335 mg of insulin polypeptide in solution, and that had been subjected to simultaneous isopropanol extraction and expanded bed chromatography (followed by Zn precipitation), 415 mg of insulin polypeptide was obtained at the end of the chromatography and Zn precipitation. Thus the yield is 124% (viz. when compared to the amount of insulin polypeptide present in solution in the fermentation broth).

EXAMPLE 11

Extraction with Methanol Followed by Isolation of Insulin Polypeptide from Fermentation Culture Broth Employing Expanded Bed Cation Exchange Chromatograph At the end of fermentation, 1 liter culture broth containing 343 mg of insulin polypeptide in solution was diluted two fold with 20 mM citrate buffer, pH 3 containing methanol at a final concentration of 20% and directly fed to an expanded bed chromatography column, Streamline 25 (25 mm×100 mm dimensions), packed with 75 ml Streamline-SP cation exchange chromatography resin (Amersham Pharmacia Biotech) and equipped with a solvent delivery system and online UV detection at 280 nm. The loading was carried out at a flow rate about 100 cm/h (three fold bed expansion of the resin). The column was then washed with 10 column volumes of 20 mM citrate buffer at pH 3.0. The resin bed was then allowed to settle. The insulin polypeptide was then eluted with 100 mM Tris HCl pH 7.5. The eluate was collected as a single fraction and the insulin polypeptide was precipitated from the eluate at pH 6.0 in presence of Zinc ions. The precipitation and subsequent drying and dissolution was carried out as described in the earlier section and incorporated herein by reference. The concentration of insulin polypeptide was estimated by RP-HPLC.

From a fermentation broth containing a total 343 mg of insulin polypeptide in solution, and that had been subjected to simultaneous methanol extraction and expanded bed chromatography (followed by Zn precipitation), 404 mg of insulin polypeptide was obtained at the end of the chromatography and Zn precipitation. Thus the yield is 118% (viz. when compared to the amount of insulin polypeptide present in solution in the fermentation broth).

EXAMPLE 12

Extraction with Dimethylformamide Followed by Isolation of Insulin Polypeptide from Fermentation Culture Broth Employing Expanded Bed Cation Exchange Chromatography At the end of fermentation, 1 liter culture broth containing 336 mg of insulin polypeptide in solution was diluted two fold with 20 mM citrate buffer, pH 3 containing dimethylformamide at a final concentration of 20% and directly fed to an expanded bed chromatography column, Streamline 25 (25 mm×100 mm dimensions), packed with 75 ml Streamline-SP cation exchange chromatography resin (Amersham Pharmacia Biotech) and equipped with a solvent delivery system and online UV detection at 280 nm. The loading was carried out at a flow rate about 100 cm/h (three fold bed expansion of the resin). The column was then washed with 10 column volumes of 20 mM citrate buffer at pH 3.0. The resin bed was then allowed to settle. The insulin polypeptide was then eluted with 100 mM Tris HCl pH 7.5. The eluate was collected as a single fraction and the insulin polypeptide was precipitated from the eluate at pH 6.0 in presence of Zinc ions. The precipitation and subsequent drying and dissolution was carried out as described in the earlier section and incorporated herein by reference. The concentration of insulin polypeptide was estimated by RP-HPLC.

From a fermentation broth containing a total 335 mg of insulin polypeptide in solution, and that had been subjected to simultaneous dimethylformamide extraction and expanded bed chromatography (followed by Zn precipitation), 376 mg of insulin polypeptide was obtained at the end of the chromatography and Zn precipitation. Thus the yield is 112% (viz. when compared to the amount of insulin polypeptide present in solution in the fermentation broth).

Table 7 compares the percentage yields of insulin that had been subjected to the different purification procedures described in examples 7, 8, 9, 10 & 11.

TABLE 8

| Insulin polypeptide isolation/purification | Loading Condition | Yield (%) |
| --- | --- | --- |
| Filtration followed by cation exchange chromatography | Citrate buffer at pH 3.0 | 75 |
| Expanded bed cation exchange chromatography | Citrate buffer at pH 3.0 | 86 |
| Insulin polypeptide extraction with isopropanol and chromatography on expanded bed cation exchange Streamline SP resin | Citrate buffer containing 20% isopropanol at pH 3.0 | 124 |
| Insulin polypeptide extraction with methanol and chromatography on expanded bed cation exchange Streamline SP resin | Citrate buffer containing 20% methanol at pH 3.0 | 118 |
| Insulin polypeptide extraction with dimethylformamide and chromatography on expanded bed cation exchange Streamline SP resin | Citrate buffer containing 20% dimethylformamide at pH 3.0 | 112 |

EXAMPLE 13

Extraction with Isopropanol Followed by Isolation of Insulin Polypeptide from Fermentation Culture Broth Employing Expanded Bed Cation Exchange Chromatography At the end of fermentation, culture broth containing 464 mg of insulin polypeptide in solution was diluted two fold with 20 mM citrate buffer, pH 3 containing isoproponal at a final concentration of 20% and directly fed to an expanded bed chromatography column, Streamline 25 (25 mm×100 mm dimensions), packed with 75 ml Streamline-SP cation exchange chromatography resin (Amersham Pharmacia Biotech) and equipped with a solvent delivery system and online UV detection at 280 nm. The loading was carried out at a flow rate about 100 cm/h (three fold bed expansion of the resin). The column was then washed with 10 column volumes of 20 mM citrate buffer at pH 3.0. The resin bed was then allowed to settle. The insulin polypeptide was then eluted with 100 mM Tris HCl pH 7.5. The eluate was collected as a single fraction and the insulin polypeptide was precipitated from the eluate at pH 6.0 in presence of Zinc ions. The precipitation and subsequent drying and dissolution was carried out as described in the earlier section and incorporated herein by reference. The concentration of insulin polypeptide was estimated by RP-HPLC.

From a fermentation broth containing a total 464 mg of insulin polypeptide in solution, and that had been subjected to simultaneous isopropanol extraction and expanded bed chromatography (followed by Zn precipitation), 575 mg of insulin polypeptide was obtained at the end of the chromatography and Zn precipitation. Thus the yield is 124% (viz. when compared to the amount of insulin polypeptide present in solution in the fermentation broth).

We claim:

1. A process for enhanced recovery of recombinant insulin comprising:
   (a) expressing the insulin in yeast, wherein the expressed insulin is secreted into the culture medium;
   (b) adding a water miscible organic solvent to the fermentation culture broth, wherein the fermentation culture broth contains the secreted insulin and the yeast, wherein the water miscible organic solvent is selected from the group consisting of ethanol, isopropanol, t-butanol, acetic acid, dimethylformamide, dimethylsulfoxide, acetonitrile, dioxan, ethylene glycol, and propylene glycol, and wherein the water miscible organic solvent optionally contains additives;
   (c) clarifying the fermentation culture broth containing the added water miscible organic solvent by centrifugation and decanting the supernatant from the pellet;
   (d) isolating the insulin from the supernatant.

2. The process of claim 1, wherein the water miscible organic solvent is isopropanol.

3. The process of claim 1, wherein the water miscible organic solvent is used at a concentration range from about 10% (v/v) to about 40% (v/v).

4. The process of claim 1, wherein the additives comprise one or more of sodium chloride, calcium chloride, arginine, aspartic acid, urea, guanidinum hydrochloride, or polyethylene glycol.

5. The process of claim 1, wherein the process is carried out at a pH range from about 2 to about 5.

6. The process of claim 1, wherein the insulin is isolated using a cation exchange chromatography in expanded bed mode.

7. The process of claim 1, wherein the yeast comprises genera *Hansenula, Saccharomyces, Pichia*, or *Kluyveromyces*.

8. The process of claim 1 further comprising
   (e) resuspending the pellet of step (c) with a miscible organic solvent selected from the group consisting of ethanol, isopropanol, t-butanol, acetic acid, dimethylformamide, dimethylsulfoxide, acetonitrile, dioxan, ethylene glycol, and propylene glycol, and wherein the water miscible organic solvent optionally contains additives;
   (f) centrifuging the resuspended pellet and decanting the supernatant;
   (g) isolating the insulin from the supernatant of step (f).

* * * * *